Aug. 22, 1967 R. H. GAST Plant Pat. 2,760
HIBISCUS PLANT
Filed May 23, 1966
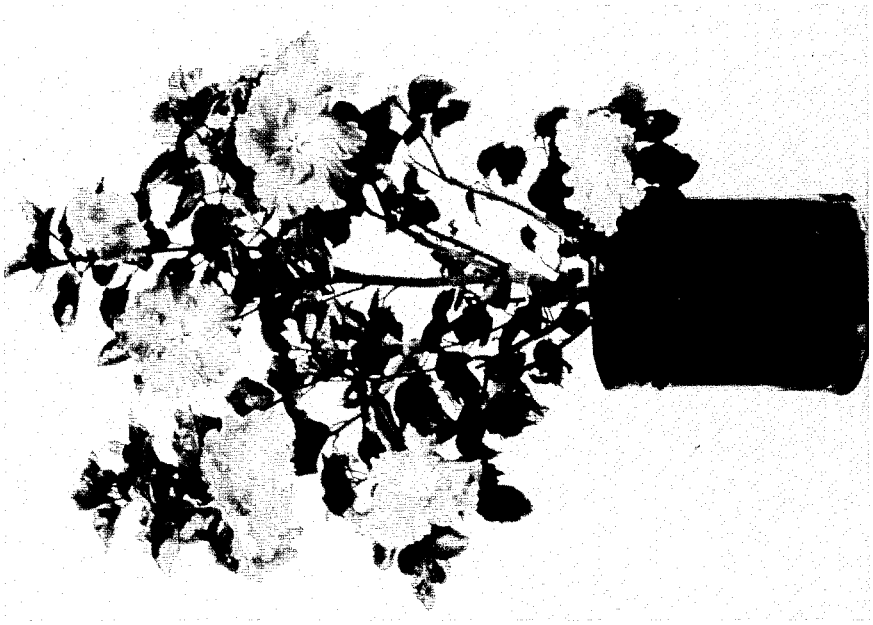
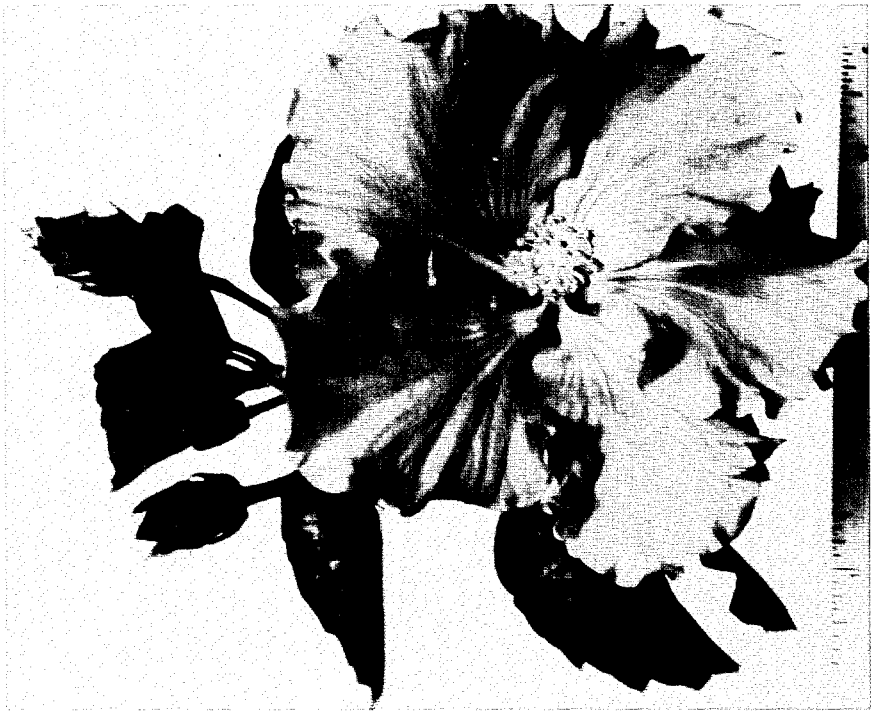
INVENTOR.
ROSS H. GAST,
By Edmond J. Shanahan
ATTORNEY.

United States Patent Office

Plant Pat. 2,760
Patented Aug. 22, 1967

2,760
HIBISCUS PLANT

Ross H. Gast, Los Angeles, Calif., assignor to Monrovia Nursery Co., Azusa, Calif., a corporation of California Filed May 23, 1966, Ser. No. 552,351
1 Claim. (Cl. Plt.—54)

The present invention relates to a new and distinct variety of hibiscus plant, of the *Rosa-sinensis* species.

The plant is characterized as to novelty by its vigorous, upright habit of growth, its crisp green foliage, and its brilliant, long-lasting flowers. A particular feature of the new variety is that the flowers will last for two days, except in very hot weather. Most hibiscus flowers last for one day only.

This plant appeared as a seedling in 1956 after extensive breeding efforts. It is not similar to any known variety. The plant will not come true from seed; it can be truly reproduced only by asexual means, that is, by grafting and cutting.

A plant and flower of the new variety are shown in full color in the accompanying illustration.

A detailed description of the new variety follows, and to facilitate identification of the important colors, the color terminology adopted by the British Horticultural Color Charts has been followed. (Reference is to "Horticultural Color Charts" issued by the British Color Council in two volumes, in collaboration with the Royal Horticultural Society, copyright by Robert F. Wilson, published 1938–41.)

*The plant*

Parentage: Seedling resulting from definite breeding efforts.

*Pollen parent.*—Shimodas Yellow.

*Seed parent.*—Gast's #282.

Growth: The plant is of vigorous upright growth, well-clothed with foliage. The ultimate height of the plant is not known, but under normal conditions it should reach a height of 6 to 8 feet, with a spread of 3 to 4 feet.

Branches: New branch growth is a light green (Scheeles Green 860), changing to a light brown as it matures. Bark is slightly rough.

Growth habit: Branching starts just above ground level and has a tendency to be ascending.

Foliage: The leaves are of good substance and are glossy.

*Shape.*—The leaves are best described as being broadly ovate, with the margin undulate and coarsely-toothed. The apex of the leaf is acuminate; the base truncate.

*Color.*—The upper surface of the leaf is Spinach Green o960; the underside is Scheeles Green 860.

*Size.*—Leaves are from 2¼ to 3¼ inches wide, and from 2¾ to 4 inches long. Petiole is 1¼ inches long.

*Arrangement.*—Leaves are alternate on the stems.

*Veins.*—The underside of each leaf has prominent veins, extending from the base of the leaf. Veins are slightly darker in color than the underside of the leaf.

*The flower*

The plant blooms in great abundance from May through October in southern California, with lighter bloom thereafter until the advent of colder weather.

Form: Flowers are slightly cup-shaped. Width varies from 6 to 7 inches across the flower.

Petals: Petals are five in number and are overlapping and ruffled, sometimes being slightly reflexed at the tips.

Color: The base of the petal is white, with a ring of China Rose o24/1 extending up about one-third of the way on each petal. The basic color of the petals is Indian Orange 713/1, with an overcast of China Rose o24/1 seen when petals are viewed at an angle. Back of the petals is a light Tan with an undertone of China Rose o24/1.

Veins: Veins are white but gradually change to Indian Orange 713/1 as they extend upwards toward the edge of the petal.

Stigma pads: Stigma pads are Indian Yellow 6/1.

Style: Style is Mimosa Yellow 602/3. Length of the style is 2¾ inches.

I claim:

A new and distinct variety of hibiscus plant, of *Rosa-sinensis* species, substantially as herein described and illustrated, and characterized particularly as to novelty by its vigorous, upright habit of growth, its crisp green foliage, and its brilliant, long-lasting flowers.

No references cited.

ABRAHAM G. STONE, *Primary Examiner.*

ROBERT E. BAGWILL, *Examiner.*